(12) United States Patent
Wolter

(10) Patent No.: US 9,883,790 B2
(45) Date of Patent: Feb. 6, 2018

(54) MEDICAL LUMINAIRE FOR BACKGROUND LIGHT AND EXCITATION LIGHT

(75) Inventor: Michael Wolter, Hamburg (DE)

(73) Assignee: OLYMPUS WINTER & IBE GMBH, Hamburg (DE)

(*) Notice: Subject to any disclaimer, the term of this patent is extended or adjusted under 35 U.S.C. 154(b) by 688 days.

(21) Appl. No.: 13/393,337

(22) PCT Filed: Aug. 5, 2010

(86) PCT No.: PCT/EP2010/004798
§ 371 (c)(1),
(2), (4) Date: Mar. 28, 2012

(87) PCT Pub. No.: WO2011/026548
PCT Pub. Date: Mar. 10, 2011

(65) Prior Publication Data
US 2012/0182754 A1    Jul. 19, 2012

(30) Foreign Application Priority Data

Sep. 4, 2009   (DE) .................. 10 2009 040 093

(51) Int. Cl.
*A61B 1/07*    (2006.01)
*A61B 1/00*    (2006.01)
(Continued)

(52) U.S. Cl.
CPC ............ *A61B 1/07* (2013.01); *A61B 1/00167* (2013.01); *A61B 1/043* (2013.01); *A61B 1/063* (2013.01); *A61B 1/0638* (2013.01); *A61B 1/0669* (2013.01); *A61B 5/0084* (2013.01); *A61B 5/0071* (2013.01)

(58) Field of Classification Search
CPC ..... A61B 1/00167; A61B 1/043; A61B 1/063; A61B 1/0638; A61B 1/0669; A61B 1/07; A61B 5/0071; A61B 5/0084
See application file for complete search history.

(56) References Cited

U.S. PATENT DOCUMENTS 6,016,435 A * 1/2000 Maruo et al. ................. 600/316
6,069,689 A   5/2000 Zeng et al.
(Continued)

FOREIGN PATENT DOCUMENTS

DE   692 20 720 T2   1/1998
DE   196 39 653 A1   4/1998
(Continued)

OTHER PUBLICATIONS

Information Sheet of Laser Endoscopy for Blood Vessel, STI-86032, The Furukawa Electric Co., Ltd., 8 pages (Feb. 1986).

*Primary Examiner* — Ruth S Smith
(74) *Attorney, Agent, or Firm* — Scully, Scott, Murphy & Pressar, P.C.

(57) ABSTRACT

A medical luminaire for photodynamic diagnosis. The medical luminaire including: a broad-band lamp for generating broad-band background light; a semiconductor lamp for generating short-wave excitation light, wherein the semiconductor lamp comprises a laser diode, the light from which is fed alternatively or additionally into a light path of the broad-band lamp, and a light fiber bundle for transporting the light, wherein the excitation light is transported in a partial bundle.

7 Claims, 2 Drawing Sheets

(51) Int. Cl.
  *A61B 1/04* (2006.01)
  *A61B 1/06* (2006.01)
  *A61B 5/00* (2006.01)

(56) References Cited

U.S. PATENT DOCUMENTS

| | | |
|---|---|---|
| 7,102,746 B2 * | 9/2006 | Zhao .......................... 356/301 |
| 7,582,057 B2 | 9/2009 | Toriya et al. |
| 7,903,338 B1 * | 3/2011 | Wach .......................... 359/588 |
| 2001/0049473 A1 | 12/2001 | Hayashi |
| 2004/0186351 A1 | 9/2004 | Imaizumi et al. |
| 2006/0051036 A1 | 3/2006 | Treado et al. |
| 2006/0184037 A1 | 8/2006 | Ince et al. |
| 2006/0190006 A1 | 8/2006 | Oka et al. |
| 2007/0203413 A1 * | 8/2007 | Frangioni .................... 600/478 |

FOREIGN PATENT DOCUMENTS

| | | |
|---|---|---|
| DE | 100 02 106 A1 | 8/2000 |
| DE | 199 02 184 C1 | 9/2000 |
| DE | 100 31 530 A1 | 1/2001 |
| DE | 100 43 162 B4 | 4/2001 |
| DE | 101 36 191 A1 | 2/2003 |
| DE | 10 2005 036 147 A1 | 2/2007 |
| DE | 10 2006 011 749 A1 | 9/2007 |
| EP | 0 512 965 A1 | 11/1992 |
| EP | 0 590 268 A1 | 4/1994 |
| JP | H10-337271 A | 12/1998 |
| JP | 2005-218760 | 8/2005 |
| WO | 2005/016118 A2 | 2/2005 |
| WO | 2009/131840 A1 | 10/2009 |

* cited by examiner

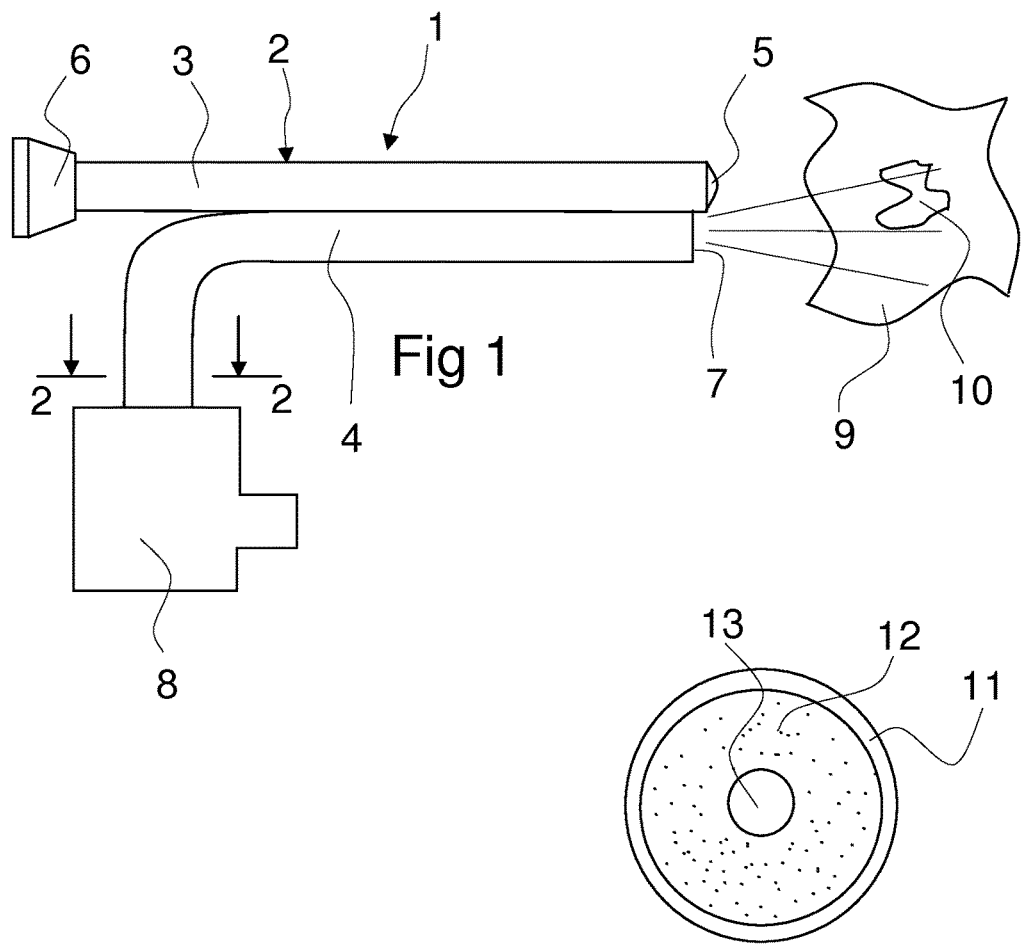
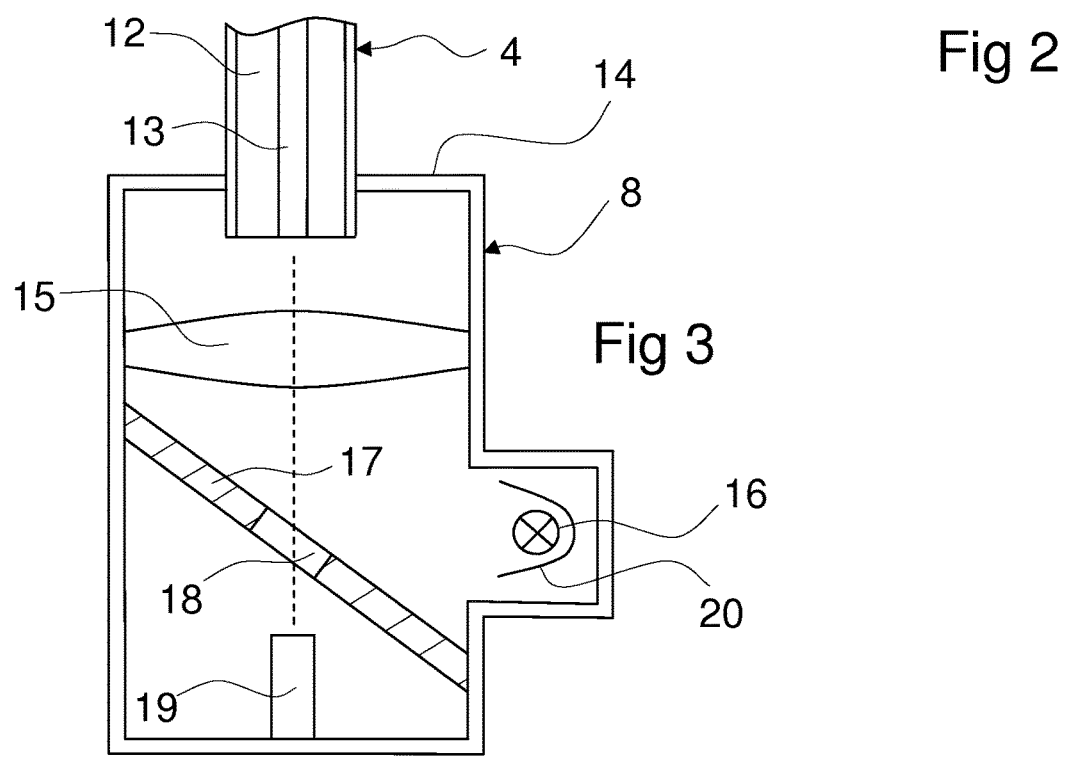

MEDICAL LUMINAIRE FOR BACKGROUND LIGHT AND EXCITATION LIGHT

CROSS-REFERENCE TO RELATED APPLICATION

The present application is based upon and claims the benefit of priority from PCT/EP2010/004798 filed on Aug. 5, 2010, which claims benefit to DE 10 2009 040 093.1 filed on Sep. 4, 2009, the entire contents of each of which are incorporated herein by reference.

BACKGROUND

Field

The present invention generally relates to a medical luminaire.

Prior Art

Photodynamic Diagnosis (PDD) is primarily used for recognition of tumors which for example fluoresce after administration of certain substances. For this purpose, luminaires are required which emit short-wave excitation light onto the area to be observed, by which the fluorescent areas are stimulated to fluoresce in the long-wave range. Observation is usually accomplished by means of a long-pass filter to suppress the short-wave excitation light. Details on this state of the art can be seen for example in DE 19902184 C1 or DE 19639653 A1.

A luminaire of this class is described in DE 10200601 1749 A1. The broad-band lamp used here is an arrangement consisting of several light emitting diodes, which together generate white light and one of which, which generates blue light, serves as the semiconductor lamp for generating the excitation light. Thus the semiconductor lamp serves both to generate the excitation light and to generate the corresponding spectral range of the broad-band light.

However, this also results in disadvantages, primarily because the semiconductor lamp in this type of design must be relatively broad-band. It therefore generates a very intense blue, outshining all other frequencies, wherein only a narrow frequency range, usable for excitation, actually excites the fluorescence. The intensive blue must be filtered out with a highly effective long-pass filter in order not to outshine the entire image, including the fluorescent effects, during observation.

Luminaires of similar class are known from DE 101 36 191 A1 and DE 93 17 984 U1 in which both the light of the broad-band lamp and the excitation light are transported together into a light guide fiber bundle. A laser diode is used as the semiconductor lamp. Thus a very simple design results.

A drawback in these designs on the other hand is that both the long-wave light and the short excitation light travel through the same glass fibers, thus through the same glass. This causes disadvantages, since the glass types are not optimally adapted to the wavelengths.

SUMMARY

The goal of the present invention consists of creating a simple and cost-effective solution to this illumination problem.

According to the invention the excitation light is transported in a separate partial bundle. This can therefore be optimized for the wavelength of the excitation light, for example may consist of quartz glass, while the remainder of the partial bundle is optimized for white light in the usual way.

A superimposed feed of the excitation light onto the broad-band light is possible in many ways, but advantageously is done with a mirror, which for example because of the angle of incidence or the different light frequencies is penetrated by the one light, while the other is reflected from it.

The selection property of the mirror in terms of one light or the other can in turn be achieved in various ways, but advantageously, in that the light that passes through penetrates the mirror in a hole. This is a particularly simple design possibility.

The partial bundle can also be integrated in the light fiber bundle or advantageously be formed outside of the light fiber bundle, e.g., completely separated from it. This can offer advantages in assembly and cross-sectional utilization.

BRIEF DESCRIPTION OF THE DRAWINGS

In the drawing, the invention is shown schematically by way of example, in which:

FIG. 1 illustrates a schematic front view of an endoscope with a luminaire according to the invention, FIG. 2 illustrates an enlarged section along line 2-2 in FIG. 1, and FIG. 3 illustrates a section through the luminaire of FIG. 1.

DETAILED DESCRIPTION

Figure 4:
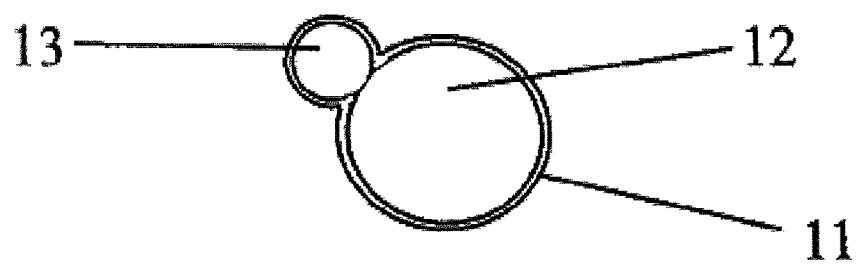
FIG. 4 illustrates a partial bundle formed outside of a light fiber bundle of a luminaire.

FIG. 1 shows an endoscope 1 in the shaft region 2 of which an image guide 3 and a fiber light guide 4 are arranged in parallel. A commonly present outer tube surrounding the image guide 3 and the fiber light guide 4, possibly also containing additional channels, has been left out of the drawing for the sake of simplicity.

The image guide 3, which for example may be designed as an image guide fiber bundle or a relay lens arrangement, at its distal end has an objective 5 and at its proximal end an eyepiece 6. Instead of the eyepiece 6 a camera may also be provided, which may also be arranged distally in the image guide 3.

The fiber light guide 4 consists of a light guide bundle, which emits light from its distal front end 7 and is supplied with light at its proximal end via a luminaire 8. The fiber light guide 4 and/or the image guide 3 can be made flexible.

The shaft region 2 of the endoscope 1 is directed against the tissue surface 9, which is shown as a cutaway in FIG. 1. On the visualized cutaway of the tissue surface 9 is a tumor 10 which is irradiated with the light from the fiber light guide 4 and viewed from the objective 5 of the image guide 3.

In the exemplified embodiment shown, the fiber light guide 4, as presented in FIG. 2, is equipped in a particular way for the transport of various light types. In the usual way, the light guide fiber bundle 12 that forms the fiber light guide 4 is positioned in a protective sleeve 11. In the light guide fiber bundle 12 a separate partial bundle 13 is shown, which is arranged centrally in the exemplified embodiment.

The partial bundle 13 can in turn be formed as a bundle of light guide fibers or consist of a single fiber. It is optimized in particular for short wave light, thus for example can consist of quartz, while the remaining bundle 12 consists of glass.

In contrast to what is shown here, the partial bundle 13 can also be formed outside of the light guide fiber bundle 12, e.g., alongside it, or located completely separately.

The interior of the luminaire 8 is shown in section in FIG. 3. The proximal end of the fiber light guide 4 is fastened in a hole in a housing 14. Through a condenser 15, which is shown schematically as a lens, the proximal face of the fiber light guide 4 is illuminated by a broad-band lamp 16 over a mirror 17 arranged at a 45° angle to the axis of the proximal end section of the fiber light guide 4. In the center, the mirror 17 has a hole 18 through with a laser diode 19 shines a narrow light bundle directly on the area of the partial bundle 13.

The laser diode 19 is designed for short wave light in the blue or ultraviolet spectrum, and in its narrow band emission spectrum, matches the absorption spectrum of a fluorescent substance administered to the tissue 9 of FIG. 1 in order to make the tumor 10 fluoresce.

In the arrangement of FIG. 3 the light generated by the laser diode 19 is transported in the partial bundle 13 separately from the light of the lamp 16, which is transported in the other cross-sectional region of the fiber light guide 4.

In a modification of the design, the fiber light guide 4 can also be made entirely of fibers of the same type, which jointly transport both types of light, thus the light of the lamp 16 and the light of the laser diode 19.

In addition the superimposition of the two light types from the lamp 16 and the laser diode 19 can be achieved in a different way than is shown, for example in that the mirror 17 is formed without a hole, but for example is permeable to the light of the laser diode 19, while it reflects the light of the lamp 16.

The lamp 16 is shown with a reflector 20. It can be a conventional broad-band lamp, e.g., a xenon lamp, or also as a semiconductor lamp, for example, it can consist of several lighted diodes which together generate broad-band, e.g., white light.

Instead of superimposing the light of the laser diode 19 on that of the broad-band lamp 16 as shown, it is also possible to work with alternating light. Instead of the mirror 17, for example, a movable mirror may be provided, which alternately allows one light or the other to pass through in the direction of the fiber image guide 4.

If a planar broad-band lamp is used, which is designed for example as a flat chip with LEDs arranged on it, it is possible to dispense with the mirror 17 and the light of the laser diode 19 may pass through a hole in the chip of the broad-band lamp.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A medical luminaire for photodynamic diagnosis, the medical luminaire comprising:
    a broad-band lamp for generating broad-band background light;
    a semiconductor lamp for generating short-wave excitation light, wherein the semiconductor lamp comprises a laser diode, the light from which is fed alternatively or additionally into a light path of the broad-band lamp, and
    a light fiber bundle for transporting the broad-band background light, wherein the laser diode is configured to emit light into the light path of the broad-band background light before entering the light fiber bundle, wherein the excitation light is transported in a partial bundle of light fibers, wherein the light fiber bundle is configured to transport the broad-band background light separately from the excitation light transported in the partial bundle of light fibers, wherein the partial bundle of light fibers is surrounded by the light fiber bundle.

2. The medical luminaire according to claim 1, wherein the excitation light is fed into the partial bundle of light fibers through a mirror and the mirror reflects the broad-band background light.

3. The medical luminaire according to claim 2, wherein the mirror has a hole that allows the excitation light through.

4. The medical luminaire according to claim 1, wherein the light fiber bundle comprises a first material and the partial bundle of light fibers comprises a second material different from the first material.

5. The medical luminaire according to claim 4, wherein the light fiber bundle comprises glass and the partial bundle of light fibers comprises quartz.

6. The medical luminaire according to claim 1, wherein the broad-band background light is transported through a lens from the broad-band lamp to a distal end of the light fiber bundle and the excitation light is transported through the lens from the semiconductor lamp to the distal end of the light fiber bundle.

7. The medical luminaire according to claim 1, wherein the partial bundle of light fibers is configured to transport the excitation light at the same time as the broad-band background light is transported in the light fiber bundle.

* * * * *